United States Patent
Perlo et al.

(10) Patent No.: US 7,297,132 B2
(45) Date of Patent: Nov. 20, 2007

(54) SHAPE MEMORY SHUTTER DEVICE

(75) Inventors: Piero Perlo, Sommaria Bosco (IT); Valentina Grasso, Carignano (IT)

(73) Assignee: C.R.F. Societa Consortile per Azioni, Orbassano (Torino) (IT)

( * ) Notice: Subject to any disclaimer, the term of this patent is extended or adjusted under 35 U.S.C. 154(b) by 46 days.

(21) Appl. No.: 11/116,227

(22) Filed: Apr. 28, 2005

(65) Prior Publication Data

US 2005/0256465 A1    Nov. 17, 2005

(30) Foreign Application Priority Data

May 3, 2004    (EP) .................................. 04425313

(51) Int. Cl.
*A61M 1/00*    (2006.01)
(52) U.S. Cl. ............................ 604/29; 604/30; 604/31; 604/32; 604/33; 604/34; 604/36; 604/37; 604/38; 604/39; 604/40; 604/41; 604/42; 623/14.13
(58) Field of Classification Search ................. 604/29, 604/30–34, 36–40, 41–42; 623/14.13, 14.03
See application file for complete search history.

(56) References Cited

U.S. PATENT DOCUMENTS

| 3,810,259 A | * | 5/1974 | Summers ..................... 600/30 |
| 4,556,050 A | * | 12/1985 | Hodgson et al. ............... 600/30 |
| 4,596,554 A | * | 6/1986 | Dastgeer ...................... 604/540 |
| 4,986,822 A | * | 1/1991 | Anderson ..................... 604/276 |
| 6,063,119 A | * | 5/2000 | Pintauro et al. .......... 623/23.66 |
| 6,440,164 B1 | * | 8/2002 | DiMatteo et al. .......... 623/1.24 |
| 6,939,332 B2 | * | 9/2005 | Perlo et al. .................. 604/328 |
| 2002/0129822 A1 | * | 9/2002 | Furukawa et al. .......... 128/887 |
| 2003/0220621 A1 | | 11/2003 | Arkinstall |

FOREIGN PATENT DOCUMENTS

| EP | 0 110 685 | 6/1984 |
| EP | 1 238 638 | 9/2002 |
| EP | 1 243 235 | 9/2002 |

* cited by examiner

*Primary Examiner*—Tatyana Zalukaeva
*Assistant Examiner*—Ginger T. Chapman
(74) *Attorney, Agent, or Firm*—Nixon & Vanderhye, P.C.

(57) ABSTRACT

A shape memory shutter device for controlling the rectum of a disabled person, comprises a section of conduit to be connected to the rectum of the disabled person, and a shutter which controls the passage through the conduit section and actuated by a shape memory actuator. The shutter comprises a plurality of petals positioned circumferentially around the conduit section and able to move between a closed and an open position. The actuator comprises shape memory wires associated to the petals which are supplied with electrical current to cause opening of the petals.

9 Claims, 6 Drawing Sheets

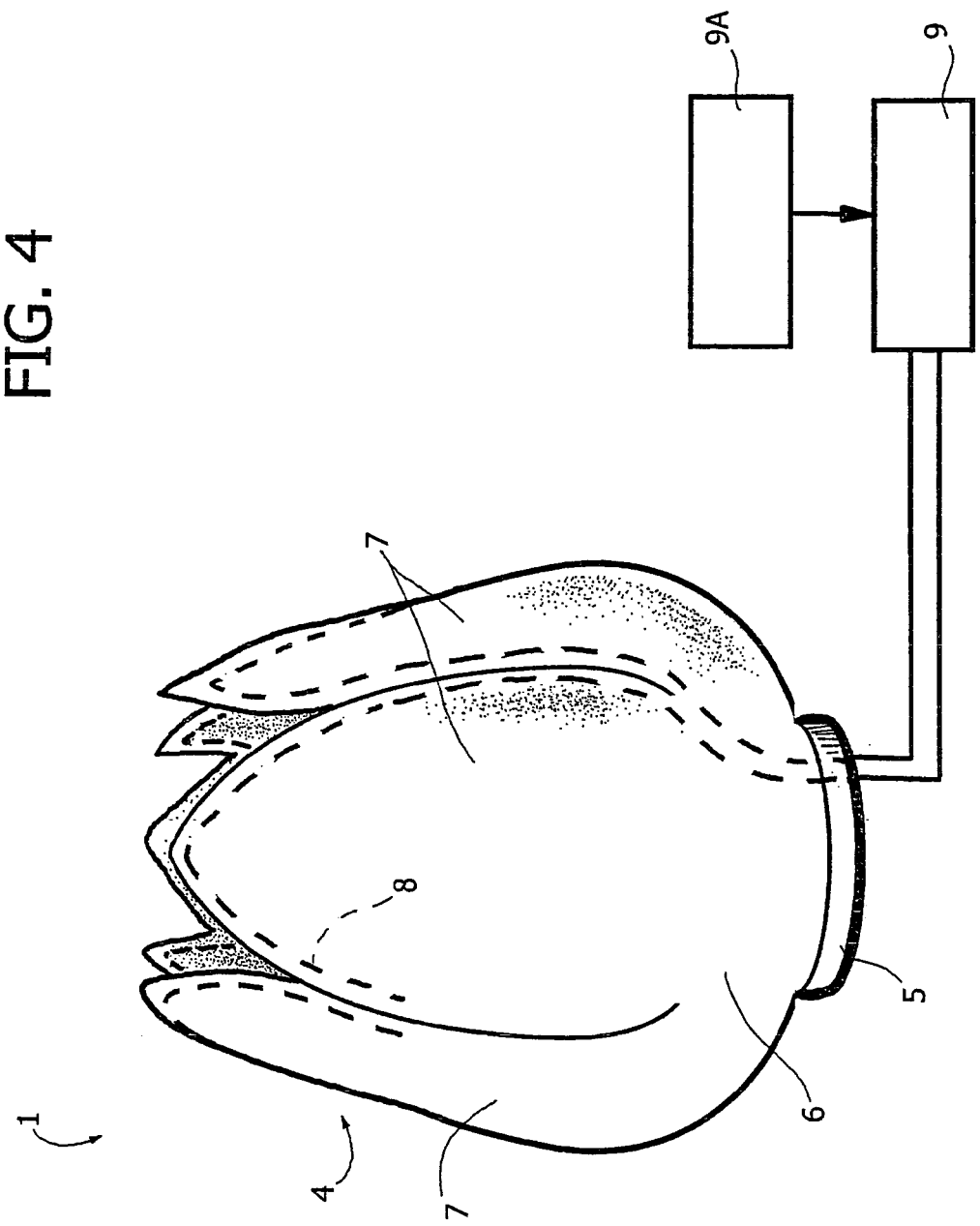

SHAPE MEMORY SHUTTER DEVICE

SUMMARY OF THE INVENTION

The present invention relates to a shape memory shutter device for controlling faecal incontinence, comprising a section of conduit to be connected to the rectum of the disabled person, shutter means which control the passage through said conduit section and shape memory actuator means for actuating said shutter means.

A shutter device of the type described above has already been proposed by the same Applicant in its European patent application EP-1 243 235 A1.

The object of the present invention is further to enhance the previously proposed device making available an additional shutter solution that has particular advantages above all in terms of simplicity, reliability, ease of use and lastly also of bio-compatibility.

The basic concept of the shutter device according to the invention is expressed in the appended claim 1. According to said concept, the aforesaid shutter means comprise a plurality of petals positioned circumferentially around the aforesaid conduit section and able to move between a closed and an open position.

The Applicant has reached this inventive intuition by observing the solutions adopted by nature to close cavities and/or opening and noting that all of such solutions have the same objective: to guarantee the continuity of the system.

The petal system of the invention is advantages with respect to systems provided with hinges, because it is more compatible with the monolithic condition achieved by nature in living organisms.

The shutter device according to the invention is designed to be positioned in correspondence with the rectal ampoule to close the anal orifice in persons affected by faecal incontinence.

An additional preferred characteristic of the shutter device according to the invention is linked to the material and to the shape of the aforesaid petals. Preferably, the material for constructing the petals is chosen from tissues of animal origin (for example bovine or swine). The preferred embodiment starts from connective tissue which is processed to deprive it of every vital component (vascularisation system). This treatment provides for tissue degradation and prevents possible allergic reactions and biological incompatibility which could lead to common rejection phenomena. Connective tissue is rich in collagen and/or elastin. The treatment whereto it is subjected allows to maintain the mechanical properties conferred to the tissue by the aforesaid proteins.

In the aforesaid preferred embodiment, the petals extend axially starting from a shared base collar. In a first solution, said collar is provided with a shape memory valve, constructed according to any of the embodiments illustrated in the previous patent application EP 1 243 235 A1 by the Applicant (see for example FIGS. 2, 3).

In a second solution, said base collar is used solely as a rigid element for anchoring the device within the rectal ampoule, whilst the shape memory actuator means comprise a plurality of shape memory wires associated to the petals, and means for supplying an electrical current to said wires.

As disclosed in the previous patent application, the electrical power supply can be obtained for example by means of a remote electrical power supply system, battery based, portable for instance on the user's belt, or alternatively by means of a mini battery power supply system.

The petals can be constructed in such a way as to be elastically deformable and to tend to return to their closed configuration thanks to their intrinsic elasticity. In this case, the shape memory wires are used to actuate the opening of the petals, against their elasticity. It is also possible to provide two shape memory wires, a first series to actuate the petals towards the open position, and a second series to actuate the petals towards the closed position.

Moreover, in a particularly preferred embodiment, inside the petals is provided a valve device constituted by a pouch with expandable orifice. It is possible to provide shape memory wires associated directly to the inner pouch, to cause its opening, in which case the opening of the petals is caused mechanically by the opening of the interior pouch, or provide shape memory wires associated to the petals to cause the opening of the petals and of the connecting elements between petals and inner pouch, so that when the petals open, the inner pouch opens as well.

Preferably, the petals are obtained from portions of animal tissue of the type mentioned above, sewed one over the other, in such a way that the stress whereto the inner pouch is subjected when it opens does not involve the outer petals. At rest, the petals fold back onto themselves. During defecation, the petals completely deploy and the orifice opens, allowing the expulsion of the faecal matter. The external part of the device is connected to the aforesaid base collar or ring which supports it in such a way as to assure, in this case as well, a gradual transmission of the stress.

The shutter device according to the invention can be used providing with a disposable containment pouch, for the collection of the faeces, if it is destined to disabled patient who are no longer able to decide autonomously (comatose or elderly patients) or to persons who have been subjected to the resection of their sigmoid-rectal segment with the installation of an external stoma. If a containment pouch is used, it can be arranged in similar fashion to the one proposed in the Applicant's prior patent application and it can be provided with a membrane which may be fitted with an activated charcoal filter to retain intestinal gases. Alternatively to activated charcoal, so-galled "getters" can be used (this is a material with a considerable contact surface, hence usually porous, which is able to aspirate and retain gases and powders and which generally reacts with gas due to its high reactivity).

The device according to the invention is instead used without a containment pouch if it is intended for disabled patients who have lost the natural excretion stimulus (marrow lesions, cancer), but are able to react directly on any actuation devices, or for persons who have lost the tone of the outer sphincter muscles, and thus do feel the stimulus, but are not able to block the passage of the faeces.

If it is intended for the latter categories of patients, who do not require the containment pouch, the device according to the invention is preferably also provided with sensor means able to detect the presence of material inside the device, for instance within the inner pouch in the case of the preferred embodiment. For this purpose, one could for example use pressure sensors associated to the walls of the inner pouch. The detection of material inside the device generates the emission of an alarm signal, whereupon the patient him/herself can positively command the activation of the shape memory actuator means to cause the opening of the shutter device. In this case, therefore, the patient him/herself decides when and where to open the device to eliminate faeces and/or gases.

The possible power supply alternative for the actuation systems used is given by "Energy Harvesting" with respect to the bloodstream. For example, implantable bio-fuel cells could be used, which electro-oxidise glucose and electro-reduce the oxygen present in the bloodstream.

BRIEF DESCRIPTION OF THE DRAWINGS

Additional characteristics and advantages of the present invention shall become readily apparent from the description FIGS. 2-4 show a first embodiment of the device according to the invention in three different operating conditions.

DETAILED DESCRIPTION OF THE INVENTION

Figure 1:
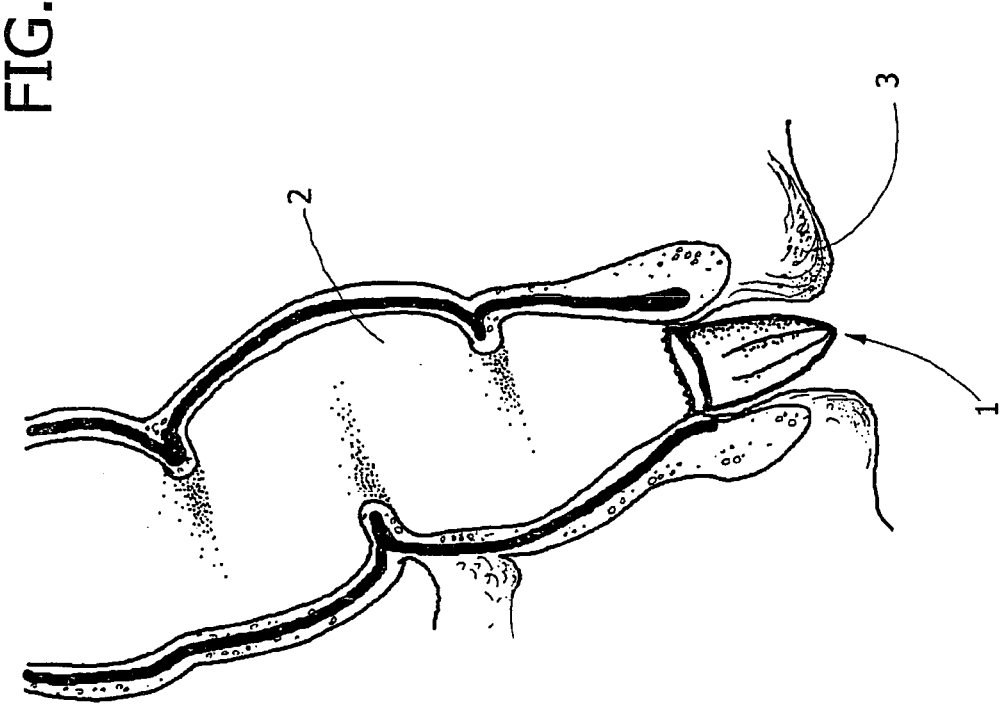
FIG. 1 is a section view showing the positioning of the device according to the invention inside the rectal ampoule.

FIG. 1 shows a device 1 according to the invention implanted in the terminal part of the rectum 2 of a disabled person, within the sphincter 3. FIG. 1 thus provides an idea of the dimensions of the device according to the invention.

Figure 3:
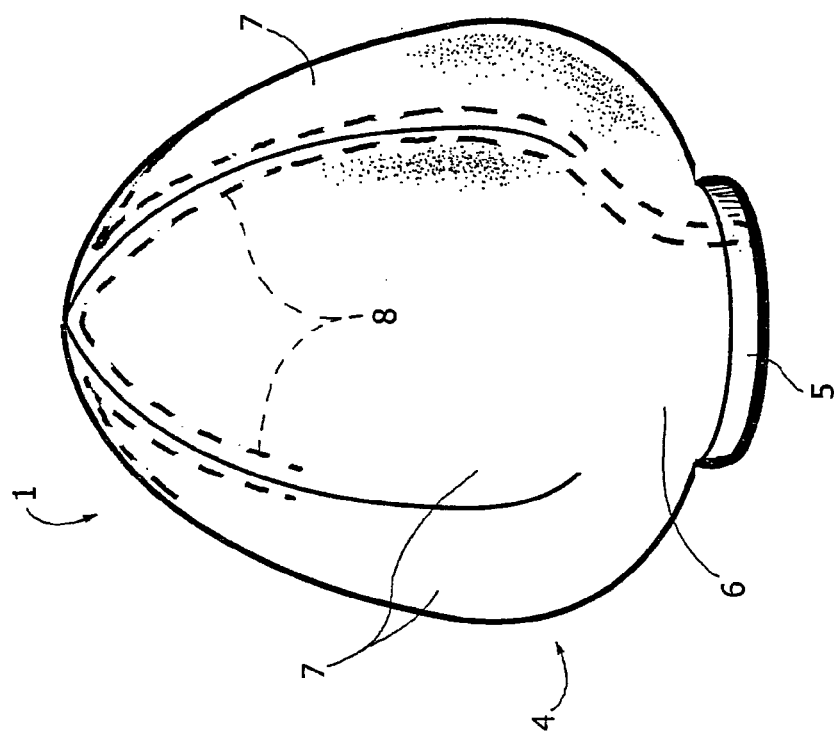
Figure 2:
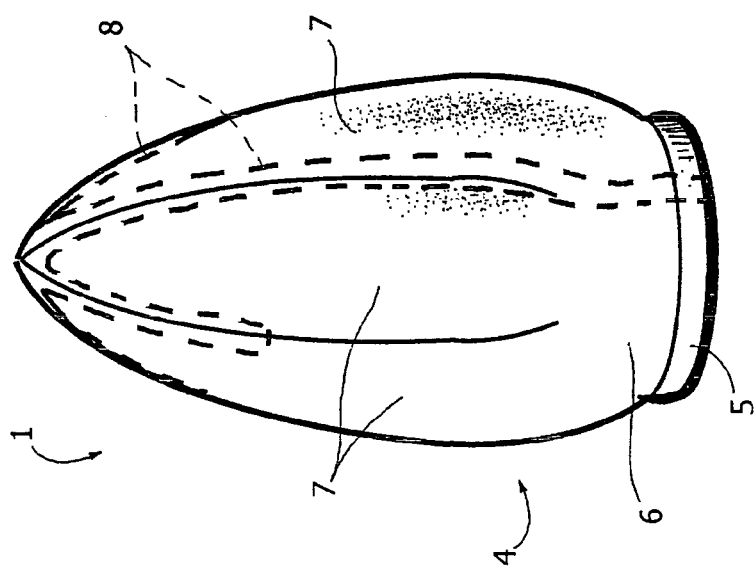

With reference to FIGS. 2-4, the device 1 comprises a body that is globally designated by the number 4, preferably constituted by animal connective tissue (for instance bovine or swine) treated to deprive it of every vital component. Naturally, this does not exclude the use of other materials, including the synthetic materials. The body 4 has a base ring or collar 5 which defines a conduit section 6 and wherefrom depart a plurality of petals 7, all extending starting from the ring 5 and movable between a closed condition (FIG. 2) and an open condition (FIG. 4).

In the illustrated example, to the petals 7 are directly associated multiple shape memory wires 8 which are connected to an electrical power supply device 9 (shown schematically in FIG. 4) able to be activated by means of a wireless remote control system from an activation device 9A controlled by the patient. The wires 8 can for example be arranged along the end edges of the petals 7 in such a way that when they are traversed by current they heat up and consequently they shorten, determining a deformation of the petals towards the open configuration.

In the structurally simplest embodiment, the petals 7 can be constructed in such a way as to be elastically deformable and to tend, because of their very elasticity, to remain in the closed configuration of FIG. 2. Alternatively, the shape memory wires could be arrange to actuate the petals towards the open condition and an additional series of shape memory wires to actuated the petals towards the closed position.

When the rectum 2 is traversed by material to be evacuated, said material is collected within the petals in the closed condition, inflating them from the configuration of FIG. 2 to that of FIG. 3. In this condition, an activation of the shape memory actuator means which actuate the opening of the petals causes the passage to the open configuration of the actuator device which is illustrated in FIG. 4.

Figure 5:
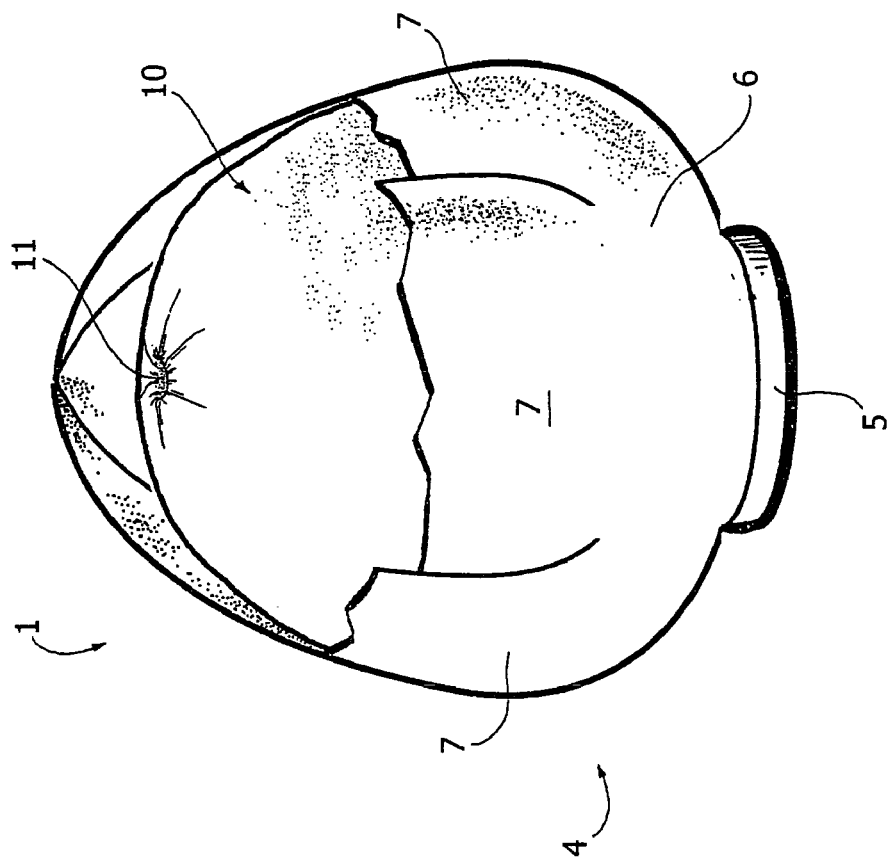
FIGS. 5, 6, 7 and 7A show a second embodiment in three different operative conditions.
Figure 6:
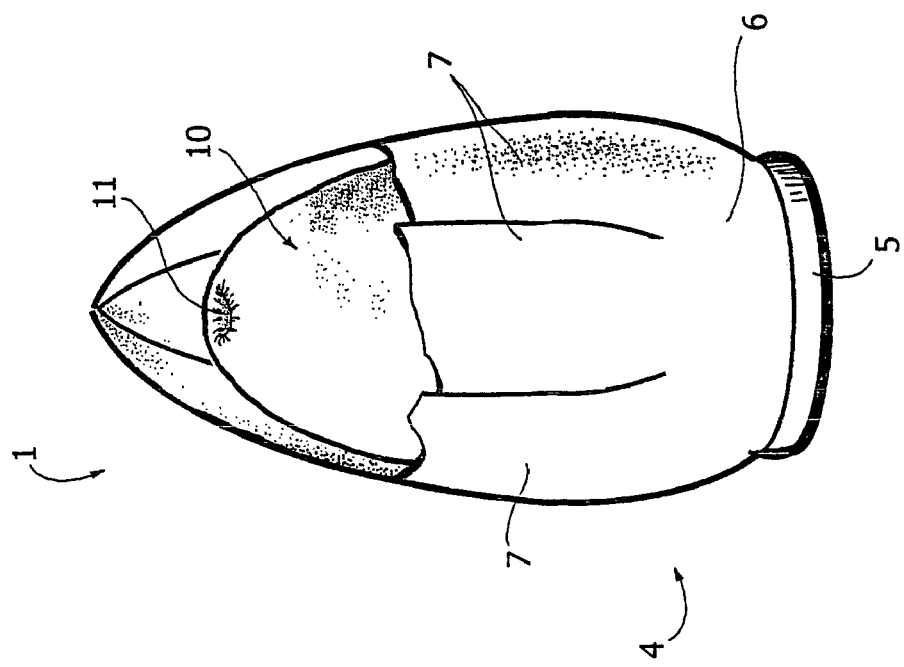
Figure 7A:
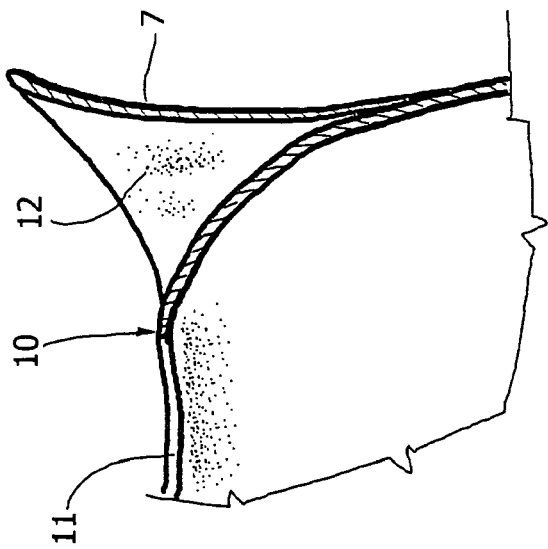
Figure 7:
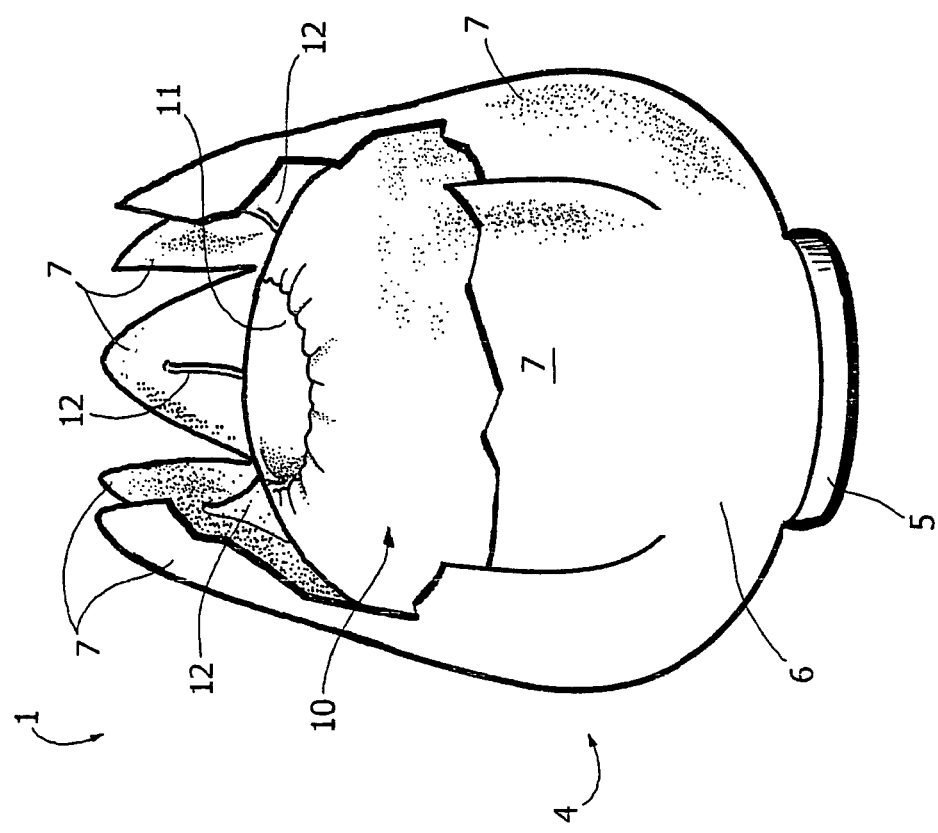

FIGS. 5-7, 7A show an additional embodiment in which in the space within the petals 8 is positioned a valve 10 constituted by a deformable pouch provided at its apex with an evacuation orifice 11. FIG. 5 shows the device in the resting condition. FIG. 6 shows the device when the pouch 10 is filled with material to be evacuated, and FIG. 7 shows the device in the evacuation condition. In one embodiment, the shape memory wires 8 are associated to the petals 7, and walls of tissue 12 are also provided, which connect each petal 7 to the wall of the pouch 10 (FIG. 7a) in such a way that the opening of the petals 7 mechanically determines also the opening of the orifice 11 of the pouch 10. However, the shape memory wires could also be associated directly to the inner pouch 10 and the outer petals 7 could open as a consequence of the opening of the pouch.

Figure 8:
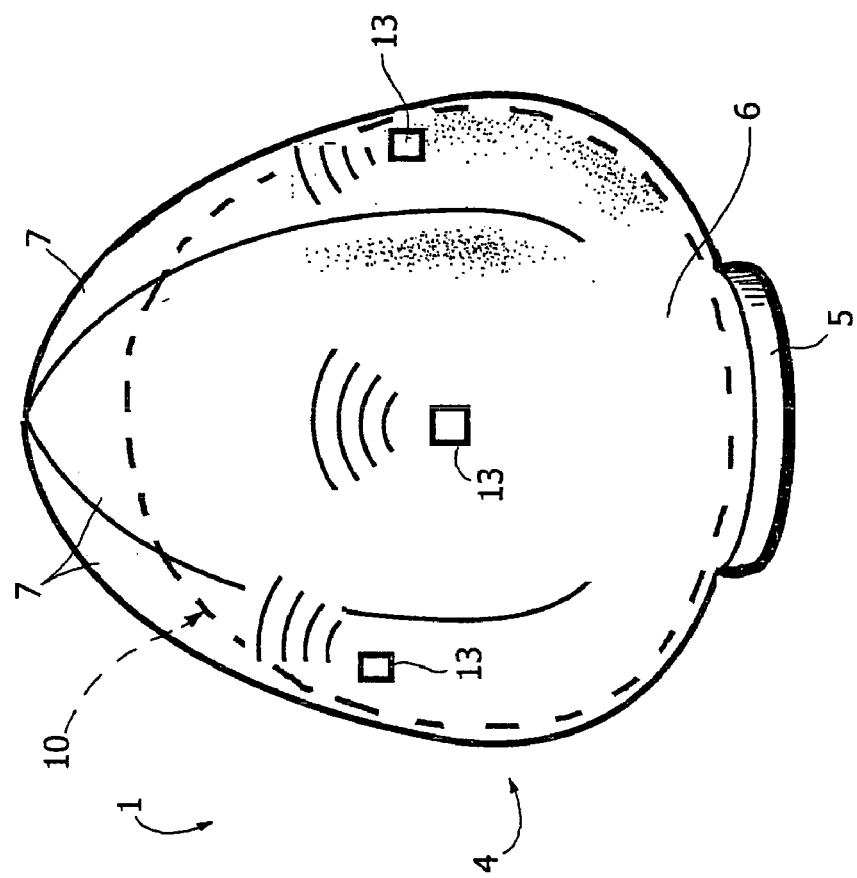
FIG. 8 shows an additional variant.

In the variant of FIG. 8 (which illustrates the device filled with material, immediately before evacuation), multiple sensors are provided (for example, pressure sensors 13 able to detect the presence of material inside the pouch and consequently to generate an alarm signal that is receivable by the patient. Upon receiving the signal, the patient can therefore positively operate the command device 9A, to command the opening of the shutter.

Naturally, without altering the principle of the invention, the construction details and the embodiments may vary widely from what is described and illustrated purely by way of example herein, without thereby departing from the scope of the present invention.

What is claimed is:

1. A shape memory shutter device for controlling the rectum of a disabled person, comprising a section of conduit to be connected to the rectum of the disabled person, shutter means which control the passage through said conduit section and shape memory actuator means for actuating said shutter means, wherein said shutter means comprise a plurality of elastically deformable walls in form of petals positioned circumferentially around said conduit section and able to move between a rest closed position and a deformed open position, wherein said shape memory actuator means comprise a plurality of shape memory wires associated to the petals and means for supplying an electrical current to said wires so as to cause heating thereof, with a resulting passage of said shape memory wires from a rest condition to an activated shortened condition which causes said petals to move to their deformed open condition, wherein within a space delimited by the petals is positioned a shape memory valve, wherein said shape memory valve comprises a pouch with an expandable discharge orifice, and wherein the shape memory actuator means are associated to the walls of the inner pouch and are able to cause the opening of the orifice when actuated, the opening of the petals being caused mechanically by the opening of the inner pouch.

2. Shutter device as claimed in claim 1, wherein the petals extend axially starting from a base collar or ring.

3. Shutter device as claimed in claim 1, wherein the petals are made of animal tissue.

4. Shutter device as claimed in claim 3, wherein the petals are made of connective tissue.

5. Shutter device as claimed in claim 4, wherein the petals are made of connective tissue from a bovine or swine.

6. Shutter device as claimed in claim 1, wherein said petals tend to return to the closed condition by effect of their elasticity.

7. Shutter device as claimed in claim 1, wherein additional shape memory wires are provided for moving the petals towards the closed condition.

8. Shutter device as claimed in claim 1, wherein it is provided with sensor means to sense the presence of material within it.

9. Shutter device as claimed in claim 8, wherein it is provided with means for generating an alarm signal following the emission by said sensor means of an output signal indicating the presence of material to be evacuated.

* * * * *